United States Patent
Kreusch et al.

(10) Patent No.: US 10,272,433 B2
(45) Date of Patent: *Apr. 30, 2019

(54) VERTICAL FUNCTIONAL REACTION VESSEL

(71) Applicant: scienova GmbH, Jena (DE)

(72) Inventors: Stefan Kreusch, Golmsdorf (DE); Raffael Rubick, Jena (DE); Claudia Macha, Dresden (DE)

(73) Assignee: Scienova GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/674,151

(22) Filed: Mar. 31, 2015

(65) Prior Publication Data

US 2016/0001285 A1  Jan. 7, 2016

(30) Foreign Application Priority Data

Mar. 31, 2014 (DE) .................. 10 2014 004 851

(51) Int. Cl.
*B01L 3/14* (2006.01)
*B01L 3/00* (2006.01)
(Continued)

(52) U.S. Cl.
CPC ........... *B01L 3/508* (2013.01); *B01L 3/50825* (2013.01); *B01L 3/50853* (2013.01); *C12M 23/00* (2013.01); *C12M 23/58* (2013.01); *C12M 29/04* (2013.01); *C12M 29/06* (2013.01); *G01N 1/4005* (2013.01); *B01L 2200/025* (2013.01); *B01L 2200/028* (2013.01); *B01L 2200/0689* (2013.01); *B01L 2300/046* (2013.01); *B01L 2300/048* (2013.01);
(Continued)

(58) Field of Classification Search
CPC ............................. B01L 3/5021; B01L 3/523
USPC .................................................. 422/548–551
See application file for complete search history.

(56) References Cited

U.S. PATENT DOCUMENTS 4,554,518 A  11/1985  Baer
7,604,739 B2  10/2009  Huang
(Continued)

FOREIGN PATENT DOCUMENTS

DE  102007011866     9/2008
DE  10 2008 017 083  10/2009
(Continued)

*Primary Examiner* — Natalia Levkovich
(74) *Attorney, Agent, or Firm* — Norris McLaughlin, P.A.

(57) ABSTRACT

A reaction vessel for a vertical operating position geometrically bits into a standard receiving vessel providing an outer volume, for example a centrifuge tube, microplates and deep well plates. The reaction vessel including at least one upper opening with a seal element for reversible sealing for typical liquid handling techniques for filling, emptying mixing and gassing; at least one upper opening for pressure balancing and overrun; and a form stable body which forms at least one non capillary reaction cavity as an inner volume with at least one semipermeable membrane as a side wall. The at least one upper opening with the seal element for reversible sealing for standard liquid handling for filling, emptying, mixing and gassing leads through at least one capillary channel in the form stable body vertically into a lower portion of the reaction vessel and forms an opening at this location.

19 Claims, 13 Drawing Sheets

(51) Int. Cl.
    *G01N 1/40*     (2006.01)
    *C12M 1/00*     (2006.01)

(52) U.S. Cl.
    CPC .......... *B01L 2300/0618* (2013.01); *B01L 2300/0681* (2013.01); *B01L 2300/0838* (2013.01); *B01L 2300/0858* (2013.01)

(56) References Cited

U.S. PATENT DOCUMENTS

| | | |
|---|---|---|
| 8,034,242 B2 | 10/2011 | Huang |
| 8,758,706 B2 | 6/2014 | Rhode et al. |
| 2003/0167031 A1* | 9/2003 | Odland ............... A61M 1/1678 604/8 |
| 2004/0171169 A1* | 9/2004 | Kallury ............... B01D 61/18 436/178 |
| 2006/0102547 A1 | 5/2006 | Huang |
| 2010/0136596 A1 | 6/2010 | Rhode et al. |
| 2010/0264085 A1 | 10/2010 | Huang |
| 2011/0163023 A1 | 7/2011 | Kreusch et al. |

FOREIGN PATENT DOCUMENTS

| | | |
|---|---|---|
| DE | 10 2009 048 039 | 6/2011 |
| EP | 0129464 | 12/1984 |
| EP | 1827659 | 9/2007 |
| WO | WO-2006/055756 | 5/2006 |
| WO | WO-2008/106960 | 9/2008 |

\* cited by examiner

Fig. 3A
Fig. 3B
Fig. 3C
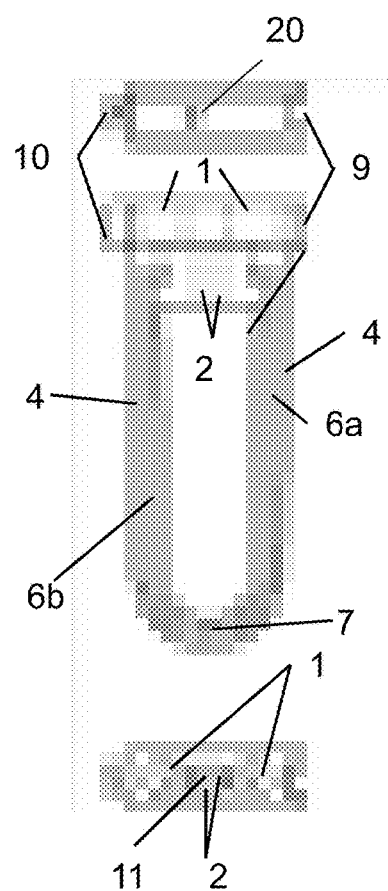
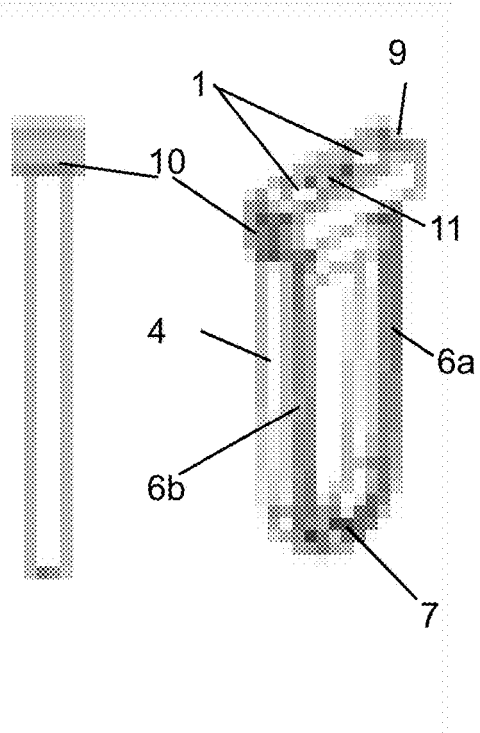
Fig. 3D

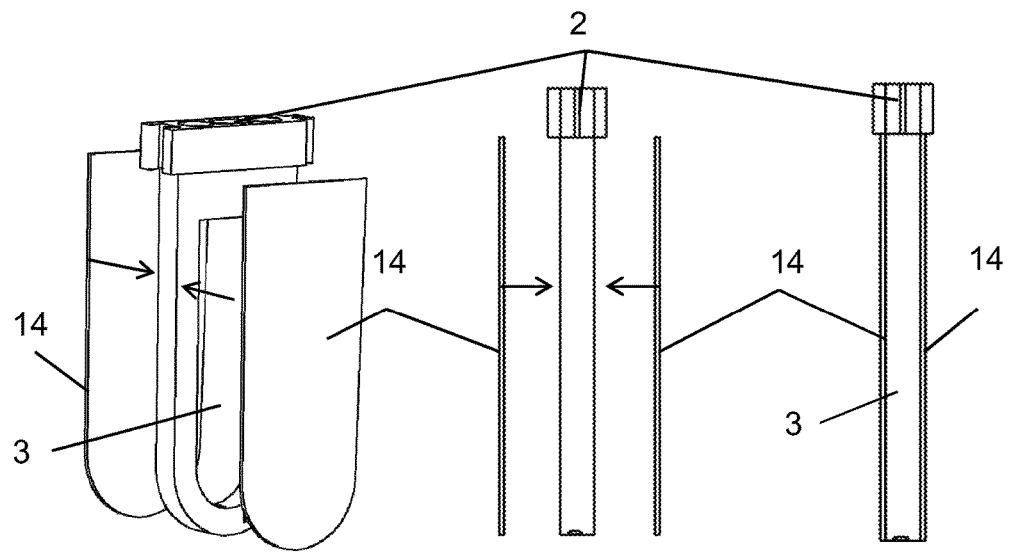

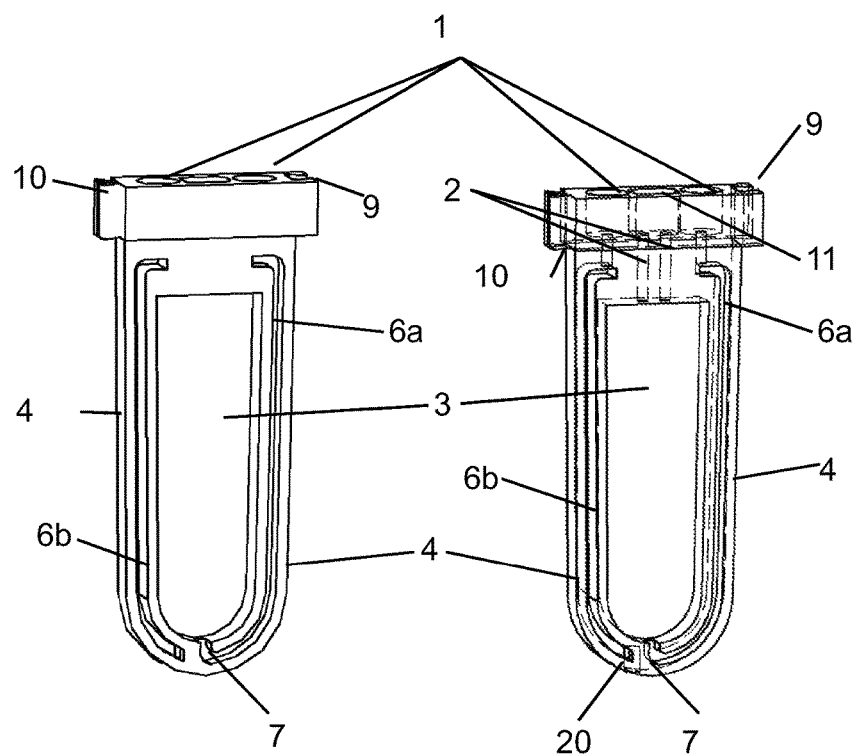

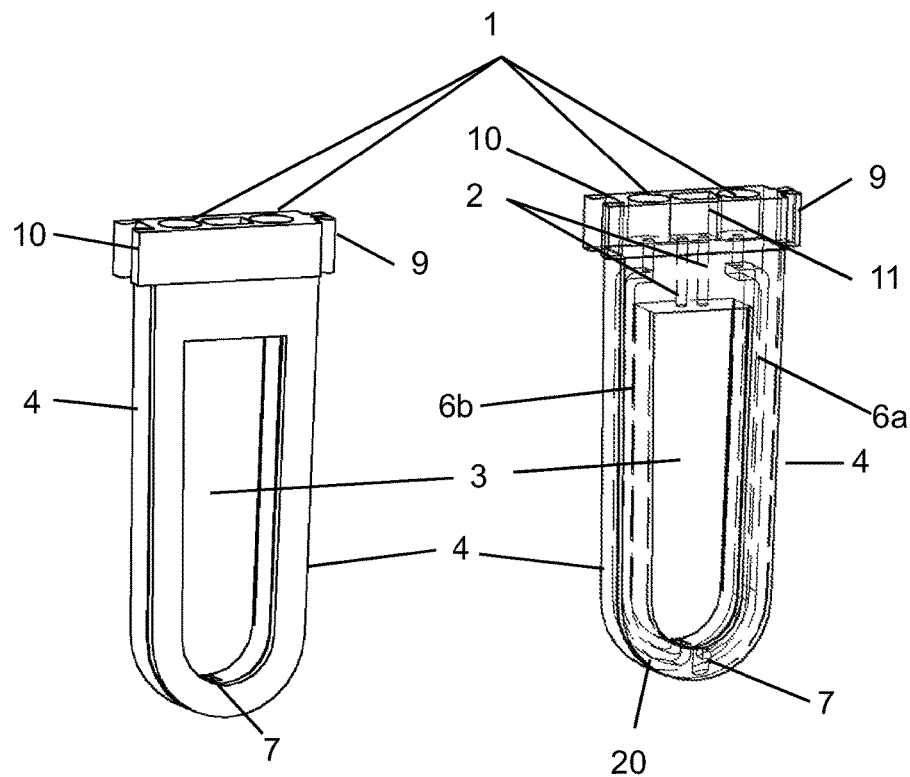

ized by quick dialysis of small volumes in dialysis capillaries. Sample introduction and retrieval of the sample volumes is performed in an upper portion of the dialysators with standard liquid handling technology. This, however, has the disadvantage that mixing in the sample cavity by dispensing is hardly practicable. The sample volume is limited by the capillary geometry that is being used for dialysis. When the capillary cross section and the capillary length increase to increase volume sample retrieval becomes more difficult since the liquid column is interrupted and air bubbles move in. When the sample volume shall be significantly increased in spite of very limited space when using vessels according to the SBS standard a new solution has to be found.

VERTICAL FUNCTIONAL REACTION VESSEL

BACKGROUND OF THE INVENTION

The Scienova Company already offers various dialysators as inserts with laterally attached semi permeable membranes for vertical use in standard deep well micro plates and centrifuge tubes (c.f.http://www.scienova.com/xanario/xpressmicrodialyzer100-c-80-2.html). They are character- When the dialysators are used as inserts the sample and the solution that is disposed in the outer vessel for example a dialysis buffer cannot be mixed, removed or exchanged anymore with pipettes or other liquid handling technology. The solution that is disposed in the outer vessel can only be changed after removing the insert. This solution is described under DE10 2007 011 866 A1, WO 002008106960 A1, US 020100136596 A1, EP 2 129 464 A1.

The Thermo Scientific Company sells a device which includes 48 individual inserts for vertical dialyzing in the micro titer plate format (c.f. herein for example www.piercenet.com/product/rapid-equilibrium-dialysis-red). These inserts are made from a plastic base element with a tube made from a dialysis membrane forming the sample cavity. The inserts are arranged in a grid of micro plates. The inserts, however, are adapted with respect to their geometry to a special outer plate for the inserts. This does not facilitate using standard vessels like deep well plates. The handling complexity is relatively high since the inserts are used individually and the special outer plate has to be dismounted and cleaned after use. Filling and emptying is performed in that pipette tips have to be run to the bottom. In particular during manual operation there is a risk that the pipette tip can damage the semi permeable membrane. The large free opening increases the contamination risk. The solution is described in WO 002006055756 A3, U.S. Pat. Nos. 7,604, 739 B2, 8,034,242 B2, US 020060102547 A1, US 020100264085 A1, EP 1 827 659 A2, EP 1 827 659 A4.

SUMMARY OF THE INVENTION

Thus, it is an object of the invention to provide a reaction vessel which forms an insert that fits vertically into standard vessels, in particular according to the recited SBS standard, which can be produced in a cost effective manner, has a sample volume range of at least 50 µl, facilitates a material exchange with the ambient through semipermeable membranes and facilitates low complexity feeding, extraction, mixing, replacing and gassing the sample volume in the reaction vessel and also in the outer volume of the outer vessel with low complexity.

The invention relates to a vertically functioning reaction vessel which is useable in a versatile manner and which fits vertically as an insert into a receiving vessel. This does not only relate to standard vessels like so called deep well plates according to the so called SBS Standard which has been defined by the society for biomolecular sciences and which has become the pertinent standard for such applications.

Semipermeable membranes facilitate a contact from an inner volume of the reaction vessel to an outer volume of the reaction vessel. Receiving vessels of this type are compatible with current liquid handling technology. Areas of application are in particular processes with sequential work charts and processes with material and volume exchange, for example in vitro protein synthesis, media exchange of protein samples and cell culture.

Air inclusions in the sample volume should only minimally affect safety of sample handling and material exchange through the semi permeable membrane. The sample retrieval should only cause low volume losses of the sample. The reaction vessel should be compatible with other liquid handling techniques like hand pipettes, pipette robots and dispensers. Its use shall be feasible in an economical and safe manner for small and also for large numbers of samples through parallel sampling processing. The invention is useable in particular but not only as a single use product for reactions that include sequential work charts with a material and volume exchange while performing mixing in a separate reaction cavity. This applies for example to enzyme reactions, chemical syntheses, non-cellular complex in vitro reactions, cell culture and sample cleaning through semipermeable membranes. Examples are proteomics work charts for sample processing, in vitro protein synthesis, product cleaning through desalinization or buffer exchange, equilibrium dialysis, electro dialysis, chemical and enzyme reactions while performing introduction and extraction of products and educts, cell cultures of eukaryotic or prokaryotic cells in a homogeneous culture or in a co-culture.

The starting point is formed by a reaction vessel for a vertical operating position, wherein the reaction vessel forms an insert that fits geometrically into a standard receiving vessel. The standard receiving vessel is used as an outer volume, for example a centrifuge tube, microplates and deep well plates. The reaction vessel has at least one upper opening with a seal element for reversible sealing for typical liquid handling techniques for filling, emptying, mixing and gassing and at least one upper opening for pressure balancing and overrun. The reaction vessel has a form stable body which forms at least one non capillary reaction cavity as an inner volume with at least one semipermeable membrane as a side wall.

According to the invention the reaction vessel is characterized in that the at least one upper opening with the seal element for reversible sealing for standard liquid handling for filling, emptying, mixing and gassing leads through at least one capillary channel in the form stable body vertically into the lower portion of the reaction vessel and forms an opening at this location.

In one embodiment the capillary channel leads from the opening with the seal element for reversible sealing for standard liquid handling for filling, emptying, mixing and gassing in the form stable body vertically into the lower portion to form an opening at this location which opening leads into the reaction cavity in the lower portion of the form stable body. Thus, the reaction cavity includes at least one semipermeable membrane as a side wall.

In another embodiment two capillary channels lead from two openings with seal elements for reversible sealing for standard liquid handling for filling, emptying, mixing and gassing in the form stable body vertically into the lower portion of the form stable body and form two openings at this location, wherein one opening leads into the reaction cavity in the lower portion and the other opening leads to an outside in the lower portion, wherein the reaction cavity has at least one semipermeable membrane configured as a side wall.

In another embodiment three capillary channels lead from three openings with seal elements for reversible sealing for standard liquid handling for filling, emptying mixing and gassing in the form stable body vertically into the lower portion and form three openings at this location wherein two openings lead into the reaction cavity in the lower portion and the other opening leads outward in the lower portion of the form stable body, wherein the reaction cavity includes at least one semipermeable membrane as a side wall.

In another embodiment two capillary channels lead from two openings with seal elements for reversible sealing for standard liquid handling for filling, emptying, mixing and gassing through two capillary channels in the form stable body vertically into the lower portion and form two openings at this location wherein the openings lead into the reaction cavity in the lower portion, wherein the reaction cavity includes at least one semipermeable membrane as a side wall.

The geometry of the reaction vessel is configured in an advantageous embodiment so that the channel opening in the outer portion is directly above the base of the receiving vessel at a distance of 0.3-3 mm, so that the channel opening is not closed by the base of the receiving vessel.

In one embodiment the capillary channels open into the lower portion of the reaction vessel and are respectively provided with fine pore frits.

The capillary channels can be formed completely by the form stable body.

However, a configuration is also feasible in which the capillary channels are formed by the form stable body and/or the semipermeable membranes on at least one side of the capillary channels.

The applied semipermeable membranes can be made from the same material and can be configured from regenerated cellulose, polyethersulfone, polyethylene, cellulose ester, silicone, or glass fibers, optionally with ion doted materials.

The applied semipermeable membranes can also be made from at least two different materials and can be respectively configured from regenerated cellulose, polyethersulfone, polyethylene, cellulose ester, silicone, or glass fibers, optionally with ion dotted materials.

In one embodiment the openings of at least two reaction vessels that are arranged in a row in bar shape are arranged in a plane in a grid of the micro plates according to SBS standard at a distance of n×9 mm for n=1 to 12.

Furthermore at least 2-24 reaction vessels can be permanently connected with one another in their upper portion in a plane and can be arranged in a grid of micro plates according to SBS Standard so that they can be inserted with their lower portion into microplates.

In one embodiment at least two reaction vessels are connected with one another with their upper portions in a plane with reversible form locking connections, e.g. dove tails or pinions and are arranged in the grid of the micro plates according to SBS standard so that they can be inserted with their lower portions into microplates.

In one embodiment the joint of the individual reaction vessels amongst each other includes a rated fracture joint which facilitates easy and defined separation.

Furthermore the reaction vessel can respectively include positioning aids in an upper portion which fixate the reaction vessel respectively within the SBS standard grid in one position in a respective well of the microplate.

The device according to the invention shall now be described in more detail with reference to exemplary embodiments.

BRIEF DESCRIPTION OF THE DRAWINGS

Illustrations are provided in FIGS. 1-13, wherein identical reference numerals are used for identical or equivalent elements, wherein:

FIGS. 3A, 3B, 3C and 3D illustrate an exemplary reaction vessel with a form stable base element and two capillary channels;

FIGS. 4A, 4B and 4C illustrate an exemplary reaction vessel with two membranes before attaching the membranes (FIGS. 4A and 4B) and after attaching the membranes (FIG. 4C);

FIG. 6 FIGS. 6A, 6B and 6C illustrate exemplary reaction vessels in a bar arrangement plugged together and including a bar in the cover and a bar in the receiving vessel of the deep well plate;

FIGS. 11A and 11B illustrate an exemplary embodiment of the base element of the reaction vessel with two capillaries in the side beam in a plain view (FIG. 11A) and in a view with hidden lines (FIG. 11B);

FIGS. 12A and 12B illustrate an exemplary embodiment of the base element of the reaction vessel with two closed capillaries in the side beam in a plain view (FIG. 12A) and in a view with hidden lines (FIG. 12B)

In the following, the numbers following, the numbers following parenthential references to figures are part numbers on the figures. The reaction vessel is adapted with respect to its geometry to standard vessels for sample treatment and storage like centrifuge tubes and in particular micro plates as receiving vessels 16 (see FIG. 1) and 17 (see; FIG. 5 and, FIG. 6) respectively. For example the reaction vessels can be configured in a form of individual centrifuge tubes, in particular as micro plates and deep well plates according to the SBS standard. The reaction vessel 15 is used as an insert (see FIG. 1) into the standard vessels 16 and 17 respectively for sample treatment and storage (see FIG. 1; FIG. 5 and FIG. 6). The standard vessel 16 and 17 respectively that is being used (see FIG. 1, FIG. 5 and FIG.

6) is subsequently designated as receiving vessel. Thus, a space remains between the wall of the receiving vessel and the insert, subsequently designated as external volume 12 (see FIG. 1), wherein the space can be filled with an external solution. The reaction vessel itself includes an inner volume 3 for sample solutions (see FIG. 1) wherein the inner volume is partially formed by a semipermeable membrane 14 functioning as a boundary relative to the outer solution in the receiving vessel (see FIGS. 4 A-C).

The semipermeable membrane 14 can be made for example from regenerated cellulose, polyethersulfone, polyethylene, cellulose ester, silicone, glass fibers, zeolites, polyamides, polycarbonates, polyacrylonitrile, polytetrafluorethylene polyvinylfluoride, polypropylene, polyvinylchloride, with ion modified materials, for example sulfonyl-, carbonyl- or amino groups as ion exchangers or with hydrophobic modifications like Cn, n=4-18. Composites of the recited materials can also be used for the membranes. They are attached at the base element of the reaction vessel by gluing, bonding or welding (see FIGS. 4A-C).

The semipermeable membranes 14 facilitate selective replacement of dissolved substances according to their properties, for example charge, hydrophobicity or size, or the passage of gasses between the inner and outer volume. Thus, different membranes 14 can also be attached at the same reaction vessel, (see FIG. 4A-C), wherein the different membranes have different selectivity and thus increase the variety of the solutions between the sample volume in the reaction vessel and the outer volume in the reaction vessel. For example, a membrane made from regenerated cellulose can be applied on one side of the reaction vessel wherein the membrane has a size selective effect and low gas permeability and on the other side a membrane made from silicone may be attached which facilitates gas transfer. A driving force of the materials transport through the semipermeable membrane is a concentration differential between outer volume and inner volume.

Figure 1:
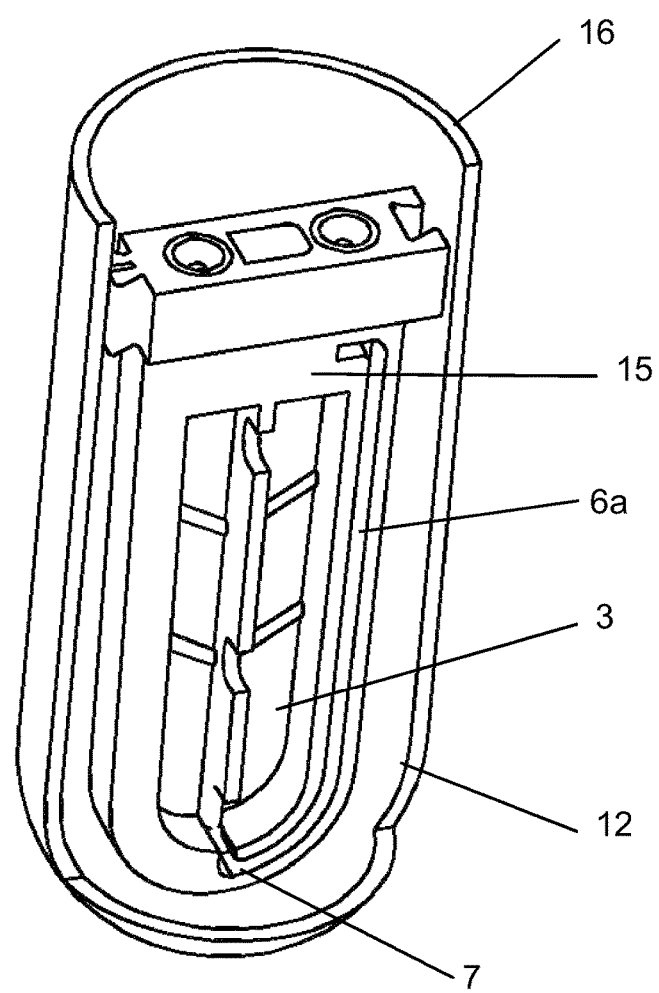
FIG. 1 illustrates an exemplary reaction vessel in a sectioned receiving vessel.

Filling the inner volume of the reaction vessel is performed from above by standard liquid handling techniques. In the upper portion the seal elements 19 are arranged in the portion of the opening 1 for filling and emptying, wherein the seal elements seal reversibly, e.g. they seal pipette tips with slight pressure (see FIG. 2A, B). Through at least one capillary 6a the sample solution or the gas is respectively pressed to the outlet opening 7 in the lower portion of the reaction vessel with slight positive pressure into the inner volume 3 (see FIG. 1). In FIG. 1 the membranes were omitted for reasons of clarity, the method of application is illustrated in FIGS. 4A-C. The upper portion of the reaction vessel includes additional pressure balancing openings 2 (see FIGS. 3A, D) so that air included in the reaction vessel can be displaced this way during filling and can flow back in when emptying is performed through vacuum extraction.

Figures 2A, 2B:
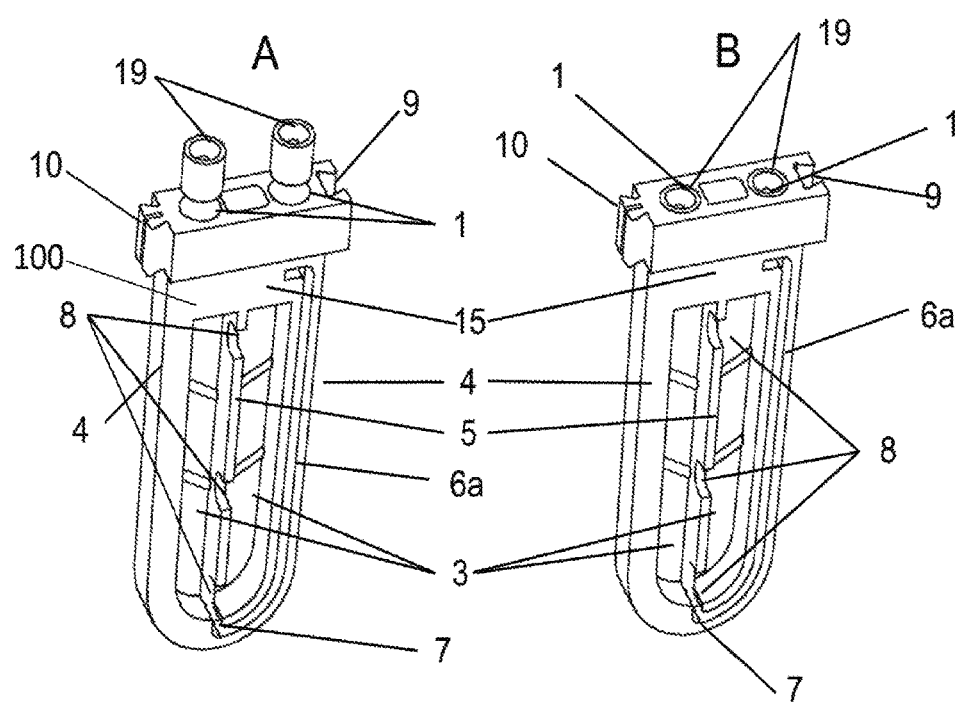
FIGS. 2A AND 2B illustrate an exemplary reaction vessel with gaskets before insertion (FIG. 2A) and after insertion (FIG. 2B) into the openings.

The outer volume 12 (see FIG. 1) is also filled by the typical liquid handling technique even before inserting the reaction vessel into the receiving vessel or can also be directly replaced with the reaction vessel inserted like in the embodiments 3, 4, and 5 of the reaction vessel described infra which include an additional opening 20 towards an outer portion and a capillary 6b which terminates at the outside at the base of the receiving vessel (see FIGS. 2A, B; FIGS. 11A, B; FIGS. 12A, B). As recited supra materials transport is performed through the semi permeable membrane and leads to a concentration gradient within the inner volume and the outer volume. This concentration gradient reduces a concentration differential directly between the respective membrane sides and thus reduces the speed of the associated materials transport.

In order to prevent a concentration gradient with in the inner or outer volume the mixing can be performed easily and safely by dispensing in the inner volume and the outer volume with a standard pipette in the embodiments 3-5 with capillaries with openings towards the inner and outer volume (see FIG. 2; FIGS. 3A-D; FIGS. 11A, B, FIG. 12B). A gassing of inner or outer volume can be performed in analogy to the described filling and emptying of the inner and outer volume through the capillaries from above. This can be performed in the simplest case by a pipette through air with slight positive pressure from the respective upper opening through the capillary into the lower portion of the opening. The gas rises in the solution in the inner or outer volume and escapes. An advantageous embodiment for gassing involves arranging a respective fine pore frit 13 in the respective lower opening 7 and 20 respectively in order to let gas bubbles flow out that are as small as possible (see FIGS. 8A, B).

Some embodiments shall be described in more detail infra. A first embodiment is a reaction vessel with a central capillary channel. The reaction vessel in this embodiment includes a base element 100 which is a form stable body and includes laterally downward extending beams 4 with a constant width of 1 mm to 5 mm and a thickness of 1 mm to 8 mm and a center strut 5 with the same thickness as the beams 4 with a capillary channel 6 that is open on one side (see FIGS. 9A, B). In the upper portion the base element is wider than the beams and includes ventilation openings 2 on both sides of the center strut 5 (see FIGS. 9A, B).

The form stable body base element is advantageously but not necessarily made from injection moldable plastic material like e.g. polystyrene, polycarbonate or polypropylene. The membrane as illustrated in FIGS. 4 A-C is mounted flush by gluing, bonding injection molding onto the membrane or by welding on the lateral beams 4 and the center strut 5 which is not illustrated in FIGS. 4A-C (see FIGS. 9A, B).

Figures 9A, 9B:
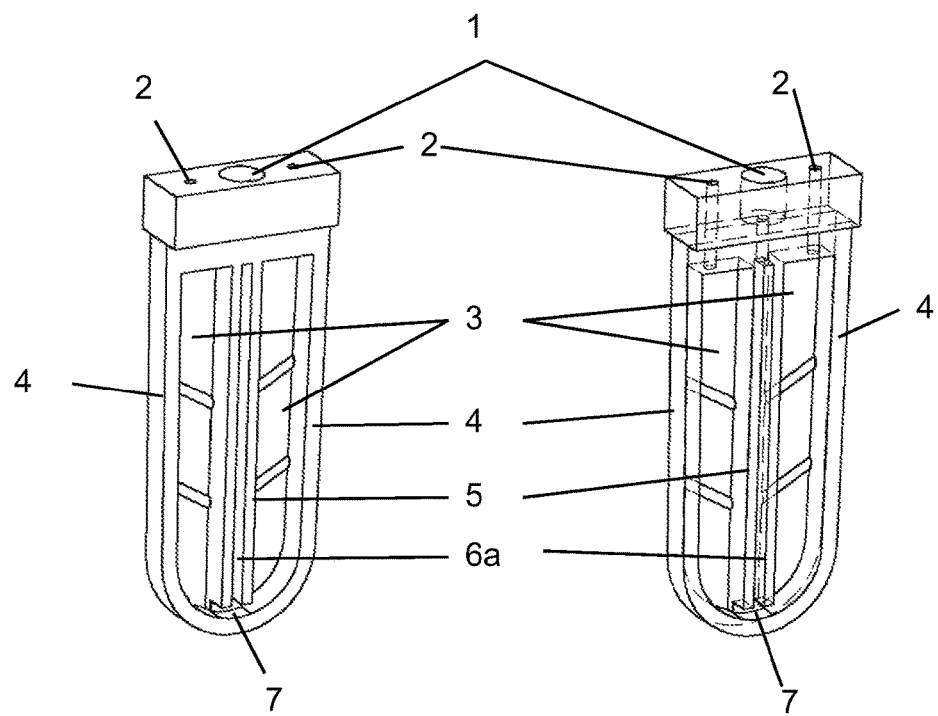
FIGS. 9A and 9B illustrate an exemplary embodiment of the base element of the reaction vessel with a capillary in a center strut in a plain view (FIG. 9A) and in a view with hidden lines (FIG. 9B)

Through the base element and the membrane placed flush thereon the inner cavity 3 is formed (see FIGS. 9A, B). The capillary channel 6a commences in the upper opening 1 for filling, emptying and mixing and terminates in the lower outlet opening 7, advantageously between 0.5 mm and 2 mm above the inner edge of the lower side in the inner volume 3 (see FIGS. 9A, B). The inner volume is in a range of 50 µl to 5000 µl. The opening 1 (see FIGS. 9A, B) is provided with a seal element 19 like in FIG. 2. The seal element 19 according to FIG. 2, provides reversible sealing of a pipette tip or pipette needle. The seal 19 according to FIG. 2 is advantageously made from a soft elastomeric material like silicone or a thermoplastic elastomeric material. The seal, however, can also be a downward tapering cone in the material of the base element with an angle of 45°-120°, advantageously 60°-50° up to 90°.

Below the opening 1 with the seal there is a tight connection with a circular cross section with a diameter between 0.2 mm and 3 mm towards the capillary channel 6a that is open on one side towards the base element with an advantageously rectangular or semi-circular cross section with a width of 0.2 mm-2 mm and a depth of 0.5 mm to 3 mm (see FIGS. 9A, B). The capillary channel 6a is closed at the open side by the applied semi permeable membrane recited supra (see FIGS. 9A, B). The semipermeable membrane (see FIGS. 4A-C) has the advantage that also the sample volume that is arranged in the capillary volume goes through a material exchange with the outer volume (see FIG. 1, 3).

The lower portion of the base element is rounded and U-shaped. The sample volume thus collects at the opening of the capillary. This lowest spot the inner volume 3 of the reaction vessel according to FIGS. 9A, B thus can be almost completely evacuated through the opening 7 and the capillary 6a (see FIGS. 9A, B). With the circular lower portion also the space in the standard receiving vessels like centrifuge tubes and deep well plates is utilized better since they typically also taper U-shaped or V-shaped. The membrane is advantageously made from regenerated cellulose but can also be made from the materials stated in the description provided supra, individually or in combination.

Another embodiment is formed by a reaction vessel with a lateral capillary channel. The reaction vessel in this embodiment is made from a form stable body base element which includes laterally downward extending beams 4 with constant width of 1 mm-5 mm and a thickness of 1 mm-8 mm with a capillary channel 6a that is open on one side in a beam 4 (see FIGS. 10A, B). In an upper portion the base element is wider than the beams 4 and includes the ventilation openings 2 (see FIGS. 10A, B). The ventilation openings terminate into an overrun portion 11 according to FIGS. 10A, B of 20 µl-200 µl. Laterally in the upper portion they are optionally provided with elements 9 and 10 that fit into each other (see FIGS. 10A, B) for a reversible form locking connection and facilitate connecting the reaction vessels with one another.

Figure 13:
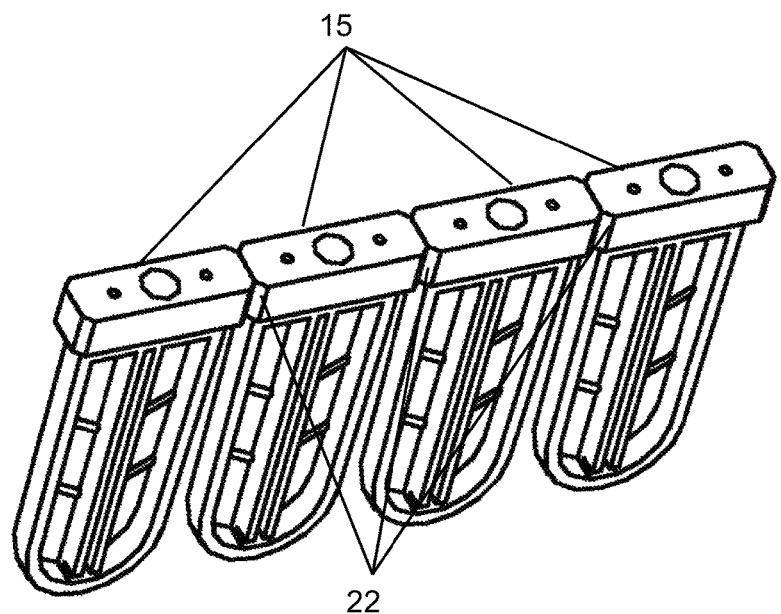
FIG. 13 illustrates an exemplary embodiment of a bar made from permanently connected base elements.

Another embodiment for connecting the reaction vessels 15 with one another through spacers 22 with rated fracture joints is illustrated in FIG. 13. The dimensions of the upper portion of the reaction vessel are advantageously configured so that the openings 1 according to FIGS. 10A, B, and lower portions of the base element 15 in the grid can be connected according to the SBS standard for microplates (see FIGS. 5A-C). Thus, they can be advantageously but not necessarily inserted into deep well microplates 17 with 48 wells according to FIGS. 5A-C and can be processed at least with 8 channel standard liquid handling technology.

The form stable body base element is advantageously but not necessarily made from injection molded plastic material like polystyrene or polypropylene. The membrane is attached flush at the lateral beams 4 by gluing, bonding, injection molding or welding. The inner cavity 3 according to FIGS. 10A, B is formed by the base element and the membrane placed flush there on. The capillary channel 6a starts in the upper opening 1 for filling, emptying and mixing and terminates in the lower outlet opening 7 in the inner volume 3 of the reaction vessel (see FIGS. 10A, B). The inner volume is in a range of 5 µl-5000 µl. The opening 1 according to FIGS. 10A, B is provided with a seal element 19 as illustrated in FIGS. 2A, B. The seal element 19 according to FIGS. 2A, B provides a reversible seal for a pipette tip or pipette needle.

The seal 19 according to FIGS. 2A, B is advantageously made from a soft elastomeric material like silicone or thermoplastic elastomeric material. The seal 19 according to FIGS. 2A, B, however, can also be a downward tapering cone in the material of the base element with an angle 45°-120° advantageously from 60°-50°-90°. Below the opening 1 (FIGS. 10A, B) there is a tight connection with a circular cross section with a diameter between 0.2 mm and 3 mm towards the capillary channel 6a that is open in the base element on one side with an advantageously rectangular or semi-circular cross section with a width of 0.2 mm-2 mm and a depth of 0.5 mm-3 mm (see FIGS. 10A, B).

Figures 10A, 10B:
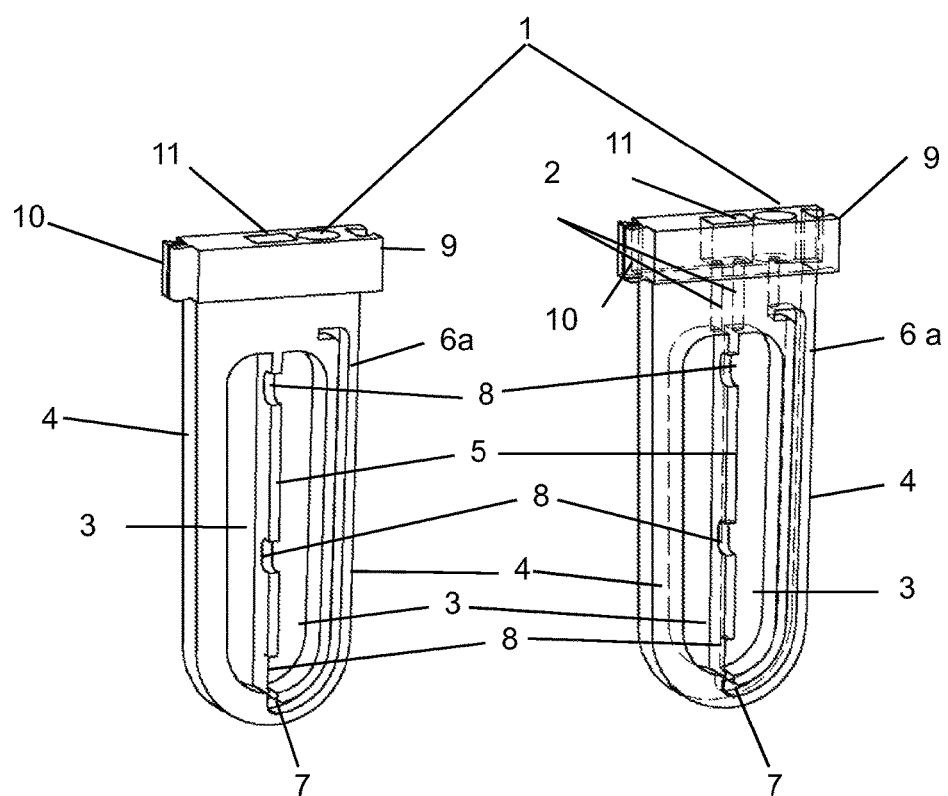
FIGS. 10A and 10B illustrate an exemplary embodiment of the base element of the reaction vessel with a capillary in a side beam in a plain view (FIG. 10A) and in a view with hidden lines (FIG. 10B)

The capillary channel 6a according to FIGS. 10A, B is closed on the open side by the applied semi permeable membrane as illustrated in FIGS. 4 A-C. The semi permeable membrane has the advantage that also the sample volume arranged in the capillary volume goes through a material exchange with the outer volume. The lower portion of the base element is rounded U-shaped. Thus the sample volume collects at the lower opening 7 of the capillary (see FIGS. 10A, B). At this lowest location the volume can be evacuated almost completely through the opening 7 and the capillary 6a (see FIGS. 10A, B). With the circular portion also the space in the receiving vessels like centrifuge tubes and deep well plates is better utilized since they typically also taper U-shaped or V-shaped. The membranes are advantageously made from regenerated cellulose but can also be made from the materials recited supra in the general description individually or in combination.

Another embodiment is formed by a reaction vessel with two lateral capillary channels closed on both sides by semi permeable membranes. In this embodiment the reaction vessel is made from a form stable body base element which has laterally downward extending beams 4 (see FIGS. 11A, B) with a uniform width of 1 mm-5 mm and a thickness of 1 mm-8 mm with two capillary channels 6a (see FIGS. 11A, B) in each beam 4 (see FIGS. 11A, B) which capillary channels are open on both sides. In the upper portion the base element is wider than the beams 4 (see FIGS. 11A, B) and includes the ventilation openings 2 (see FIG. 11B). The ventilation openings terminate in an overrun portion 11 according to FIGS. 2A, B of 20 µl-200 µl.

Laterally in the upper portion, optionally elements 9 and 10 (see FIGS. 11A, B) that fit into each other are provided to provide a reversible form locking connection and facilitate connecting the reaction vessels with one another. Another embodiment for connecting the reaction vessels 15 according to FIG. 13 with spacers including rated fracture joints 22 is illustrated in FIG. 13. The dimensions of the upper portion of the reaction vessel are advantageously provided so that the openings 1 according to FIGS. 11A, B, and lower portions of the base element 15 can be connected with each other in the grid according to the SBS standard for microplates according to FIGS. 5A-C. Thus, the reaction vessels can be advantageously but not necessarily inserted in deep well microplates 17 with 48 wells according to FIGS. 5A-C and can be processed at least with 8 channel standard liquid handling technology.

The form stable body base element is advantageously but not necessarily made from an injection moldable plastic material like polystyrene or polypropylene. The membrane is attached flush through gluing, bonding, integral injection molding or welding on the lateral beams 4 (see FIGS. 11A, B). The base element and the membrane placed flush thereon form the inner cavity 3 according to FIGS. 11A, B.

The capillary channel 6a starts in the upper opening 1 for filling, emptying and mixing and terminates in the lower outlet opening 7 in the inner volume 3 of the reaction vessel (see FIGS. 11A, B). The second capillary channel 6b is arranged in the opposite beam 4 (see FIGS. 11A, B). The capillary channel 6b starts below the opening 1 according to FIGS. 11A, B with gasket in the upper portion and terminates in an opening 20 in the lower portion according to FIG. 11B. Thus, the outer volume can be filled through this channel with a solution, a solution can be suctioned out of the outer volume, a solution can be mixed in the outer volume by dispensing or samples can be extracted.

Figures 8A, 8B:
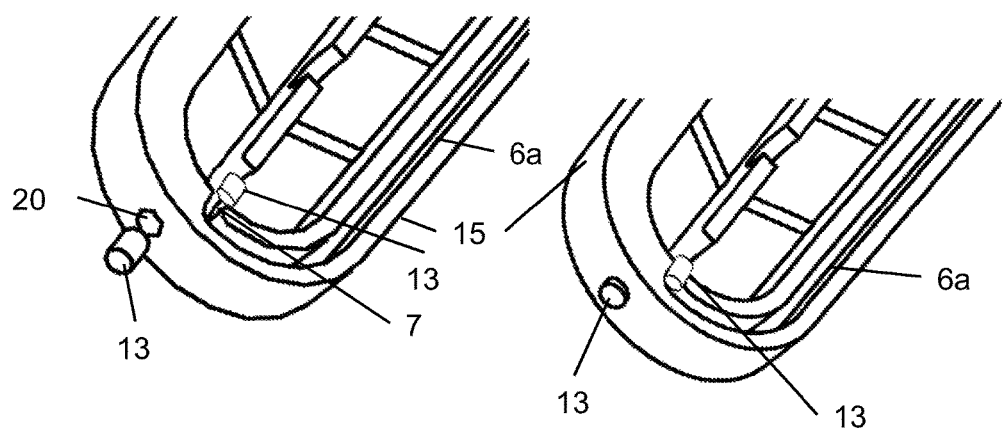
FIGS. 8A and 8B illustrate an exemplary embodiment of the reaction vessel in a lower portion before (FIG. 8A) and after (FIG. 8B) inserting frits.

Gassing the outer volume can be performed with a slight positive pressure through the capillary 6b according to FIGS. 11A, B, in particular when the opening 20 according to FIG. 11B is additionally provided with a frit 13 according to FIGS. 8A, B. Advantageously, a longitudinal dimension of the base element is selected so that the opening towards the outlet vessel is slightly above the base of the respective receiving vessel 17 according to FIGS. 5A-C and, FIG. 6C and the receiving vessel 16 according to FIG. 1, respectively.

The inner volume 3 of the reaction vessel according to FIGS. 11A, B is in a range of 50 µl to 5,000 µl. The openings 1 according to FIGS. 11A, B are provided with seal elements 19 as illustrated in FIG. 2. The seal elements (FIGS. 2A, B, 19) provide for a reversible seal for a pipette tip or a pipette needle. The seal (FIGS. 2A, B, 19) is typically made from a soft elastomeric material like silicon or a thermoplastic elastomeric material. The seal (FIG. 2, 19), however, can also be a downward tapering cone in the material of the base element with an angle of 45 degrees to 120 degrees, advantageously of 60 degrees up to 50 degrees to 90 degrees.

Below the openings 1 (FIGS. 11A, B, 1) there is a close connection with circular cross-sectional diameter between 0.2 mm and 3 mm to the capillary channels 6a, 6b that are configured in the base element in the beams 4 and open on both sides with an advantageously rectangular or semicircular cross-section with a width of 0.2 mm to 2 mm and a depth of 0.5 mm to 3 mm (see FIGS. 11A, B). The capillary channels 6a according to FIGS. 11A, B are closed on the open side by the recited applied semi-permeable membranes as illustrated in FIGS. 4A-C. The semi-permeable membrane has the advantage that the sample volume disposed in the capillary volume also goes through a material exchange with the outer volume.

The lower portion of the base element is U-shaped and rounded. Thus the sample volume collects at the lower opening 7 of the capillary according to FIGS. 11A, B. At this lowest spot, the volume can thus be almost completely suctioned through the opening (FIGS. 11A, B, 7) and the capillary (FIGS. 11A, B, 6a). With the round element also the space in the receiving vessels like centrifugation tube and deep well plates is utilized better since the receiving vessels typically also taper in U-shape or V-shape. The membranes are advantageously made from regenerated cellulose but can also be made from the materials provided supra in the general description individually or in combination.

Another embodiment is formed by a reaction vessel with two lateral capillary channels arranged on respective sides and closed by semi-permeable membranes. The reaction vessel is made in this embodiment from a form stable body base element which includes laterally downward extending beams 4 with uniform width of 1 mm to 5 mm and a thickness of 1 mm to 8 mm with two capillary channels 6a, 6b that are respectively arranged in one beam 4 and open on one side (see FIGS. 2A, B). The center strut 5 has the same thickness as the beams 4 and includes cutouts 8 (see FIGS. 2A, B). In the upper portion the base element is wider than the beams 4 according to FIGS. 2A, B and includes the ventilation openings 2 according to FIGS. 3A, D. The ventilation openings terminate in an overrun portion 11 (see FIG. 3A, 3C) of 20 µl to 200 µl. In a lateral upper portion the reaction vessels are optionally provided with elements that fit into each other (FIGS. 2A, B, 9 and 10) for a reversible form locking connection and facilitate connecting the reaction vessels with each other.

Another optional configuration for connecting the reaction vessels 15 is through spacers 22 with rated fracture joints (see FIG. 13). The dimensions of the upper portion of the reaction vessel are advantageously provided so that the openings 1 in the upper portion according to FIGS. 2A, B and the lower portions of the base element 15 can be connected with each other in the grid according to the SBS standard for microplates according to FIGS. 5A-C. Thus, the reaction vessels can be advantageously but not necessarily inserted in deep well microplates 17 with 48 wells according to FIGS. 5A, B and can be processed with multi-channel standard liquid handling technology, e.g. eightfold pipette devices.

The form stable body base element is advantageously but not necessarily made from an injection moldable plastic material like polystyrene or polypropylene. The membrane 14 is connected flush through gluing, bonding, injection molding or welding on the lateral beams 4 and the center strut 5 (see FIGS. 2A, B). The inner cavity 3 according to FIGS. 2A, B is formed by the base element and the membrane placed flush thereon. The capillary channel 6a (FIGS. 2A, B, 6a) starts in the upper opening 1 for filling, emptying and mixing and terminates in the lower outlet opening 7 in the inner volume 3 of the reaction vessel (see FIGS. 2A, B). The second capillary channel 6b is arranged in the opposite beam 4 (see FIGS. 2A, B). The capillary channel 6b starts below the opening 1 with a seal in the upper portion and terminates in an opening 20 in the lower portion (see FIGS. 2A, B). Thus the outer volume can be filled through this channel with a solution, a solution can be suctioned out of the outer volume, a solution in the outer volume can be mixed through dispensing or samples can be extracted.

Gassing the outer volume can be performed with slightly positive pressure through the capillary 6b according to FIGS. 2A, B in particular when the opening 20 according to FIGS. 2A, B is additionally provided with a frit 13 according to FIGS. 8A, B. Advantageously the longitudinal dimension of the base element is selected so that the opening towards the outlet vessel is slightly above the base of the respective receiving vessel 17 according to FIGS. 5B, C, FIG. 6C and the receiving vessel 16 according to FIG. 1 respectively. The inner volume 3 of the reaction vessel according to FIGS. 2A, B is in a range of 50 µl to 5,000 µl. The openings 1 according to FIGS. 2A, B are provided with seal elements 19 according to FIGS. 2A, B. The seal elements 19 according to FIGS. 2A, B provide reversible sealing for a pipette tip or pipette needle. The seal 19 according to FIGS. 2A, B is advantageously made from a soft elastomeric material like silicon or a thermoplastic elastomeric material. The seal 19 according to FIGS. 2A, B, however, can also be a downward tapering cone in the material of the base element with an angle of 45 degrees to 120 degrees, advantageously of 60 to 50 to 90 degrees. Below the openings 1 according to FIGS. 2A, B there is the tight connection with circular cross-section diameter between 0.2 mm and 3 mm to the capillary channels 6a, 6b according to FIGS. 2A, B that are arranged in the beams 4 according to FIGS. 2A, B and are open on both sides and advantageously have a rectangular or semicircular cross-section with a width of 0.2 mm to 2 mm and a depth of 0.5 mm to 3 mm.

The capillary channels 6a according to FIGS. 2A, B are closed on the open side by the applied semi-permeable membranes recited supra as illustrated in FIG. 4A-C. The semi-permeable membrane has the advantage that also the sample volume arranged in the capillary volume goes through a material exchange with the outer volume. The lower portion of the base element is U-shaped and rounded. The sample volume thus collects at the lower opening 7 of the capillary according to FIGS. 2A, B. At this lowest location, the volume can thus be almost completely evacuated through the opening 7 and the capillary 6a (see FIGS.

2A, B). Due to the round portion, also the space in the receiving vessels like centrifuge tubes or deep well plates is utilized better since they typically also taper U-shaped or V-shaped. The membrane is advantageously made from generated celluloses, but can also be made from the materials listed in the general description provided supra individually or in combination.

Another embodiment is configured as a reaction vessel with two lateral and closed capillary channels. The reaction vessel in this embodiment is made from a form stable body base element which includes lateral downward extending beams 4 with uniform width of 1 mm to 5 mm and a thickness of 1 mm to 8 mm with two closed capillary channels 6a, 6b in both beams 4 (see FIGS. 12A, B). In the upper portion, the base element is wider than the beams 4 according to FIGS. 12A, B and includes the ventilation openings 2 according to FIG. 12B. The ventilation openings terminate in an overrun portion (FIG. 12B, 11) of 20 µl up to 200 µl. The reaction vessels are optionally provided in their lateral upper portions with elements 9 and 10 according to FIGS. 12A, B that fit into each other for a reversible form locking connection which facilitates connecting the reaction vessels with each other. Another embodiment for connecting the reaction vessels 15 with one another by spacers with rated fracture joints 22 is illustrated in FIG. 13.

Figure 5A:
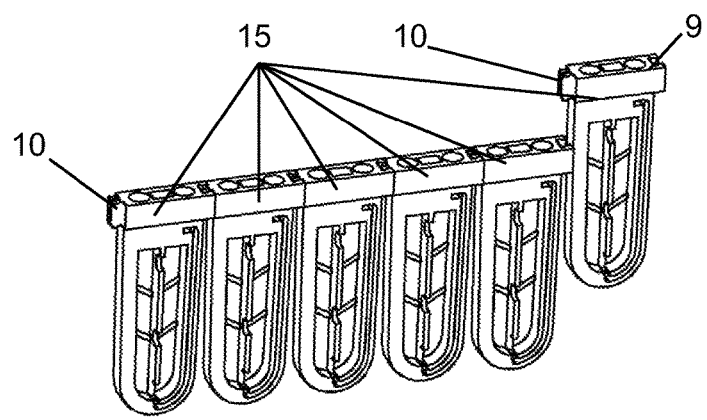
FIGS. 5A, 5B and 5C illustrate exemplary reaction vessels in a bar arrangement including a receiving vessel configured as a deep well plate.
Figure 5B:
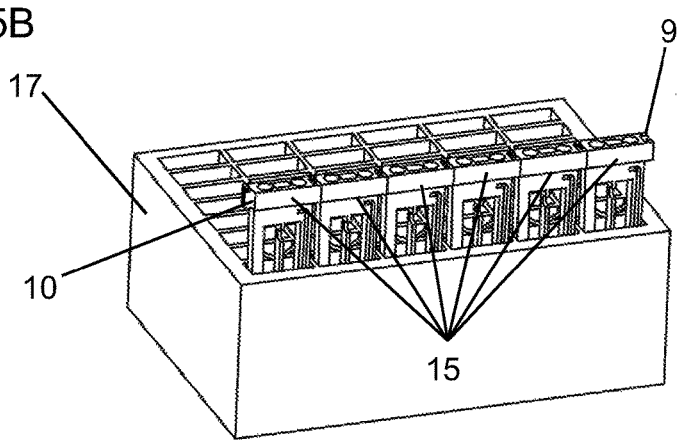
Figure 5C:
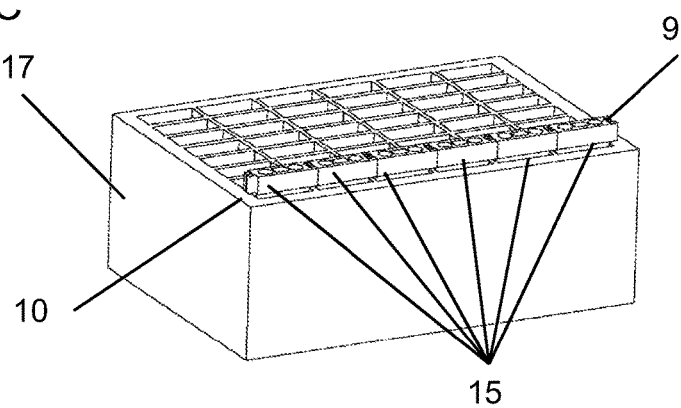

The dimensions of the upper portion of the reaction vessel are advantageously selected so that the openings 1 according to FIGS. 12A, B and lower portions of the base element 15 can be connected amongst each other in the grid according to the SBS standard for microplates according to FIGS. 5A-C. Thus, they can be advantageously but not necessarily employed in deep well microplates 17 with 48 wells (see FIGS. 5B, C) and can be processed at least with 8 channel standard liquid handling technology. The form stable body base element is advantageously but not necessarily made from injection moldable plastic material like polystyrene or polypropylene. The membrane is attached on the lateral beams 4 according to FIGS. 12A, B flush through bonding, injection molding or welding. The base element and the membrane arranged flush thereon form the inner cavity 3 according to FIG. 12. The capillary channel 6a according to FIG. 12B, starts in the upper opening 1 according to FIGS. 12A, B for filling, emptying and mixing and terminates in the lower outlet opening 7 according to FIGS. 12A, B, in the inner volume 3 (see FIG. 12), of the reaction vessel. The second capillary channel 6b according to FIG. 12B, is arranged in the opposite beam 4 according to FIGS. 12A, B. The capillary channel 6b according FIG. 12B starts below the opening 1 according to FIG. 12A, B with seal in the upper portion and terminates in an opening 20 in the lower portion (se FIG. 12B). Thus, the outer volume can be filled through this channel with a solution, a solution can be suctioned out of the outer volume, a solution in the outer volume can be mixed by dispensing or samples can be extracted.

Figure 6A:
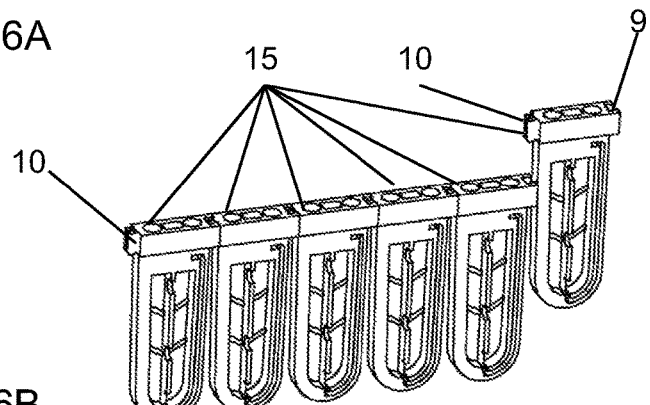
Figure 6B:
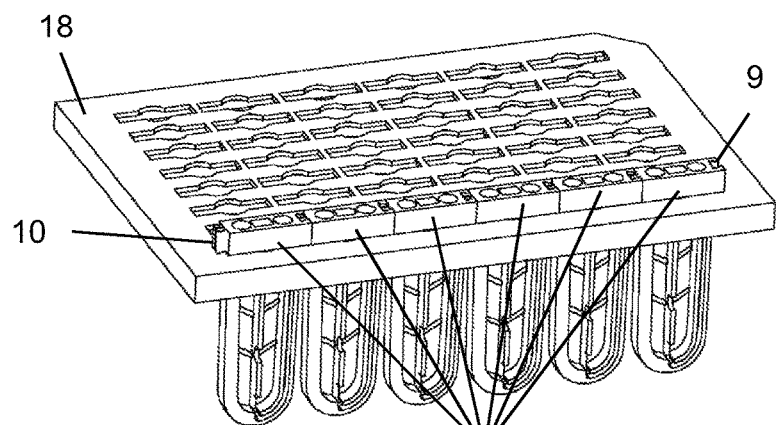
Figure 6C:
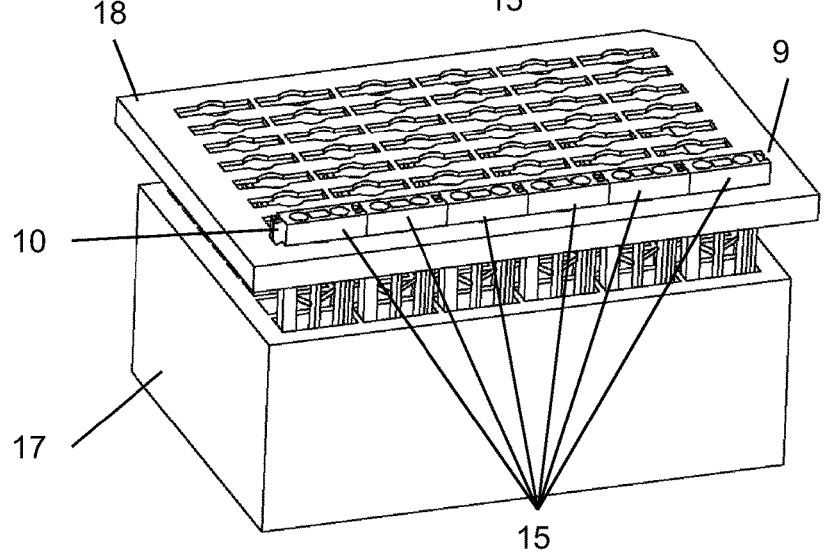

Gassing the outer volume can be performed with a slight positive pressure through the capillary 6b (see FIG. 12B), in particular when the opening 20 according to FIG. 12B is additionally provided with a frit 13 according to FIGS. 8A, B. Advantageously the longitudinal dimension of the base element is selected so that the opening towards the outlet vessel is slightly above the base of the respective receiving vessel 17 according to FIGS. 5B, C; FIG. 6C and the receiving vessel 16 according to; FIG. 1. The inner volume of the reaction vessel (FIGS. 12A, B, 3) is in a range of 50 µl to 5,000 µl.

The openings 1 are provided with seal elements 19 (illustrated in FIGS. 2A, B). The seal elements 19 according to FIGS. 2A, B provide a reversible seal for a pipette tip or a pipette needle. The seal 19 (see FIGS. 2A, B), is advantageously made from a soft elastomeric material like silicon or a thermoplastic elastomeric material. The seal 19 according to FIGS. 2A, B, however, can also be configured as a downward tapering cone in the material of the base element having an angle of 45 degrees to 120 degrees, advantageously an angle of 60 degrees to 50 degrees to 90 degrees. Below the openings 1 according to FIGS. 12A, B, the tight connection with the circular cross-sectional diameter between 0.2 mm and 3 mm is arranged towards the capillary channels that are open on both sides, arranged in the base element in the beams 4 in FIGS. 12A, B, wherein the capillary channels 6a, 6b according to FIG. 12B advantageously have a rectangular or semicircular cross-section with a width of 0.2 mm to 2 mm and a depth of 0.5 mm to 3 mm.

The lower portion of the base element is U-shaped and rounded. Thus, the sample volume collects at the lower opening 7 of the capillary (see FIGS. 12A, B). At this lowest location, the volume can be almost completely suctioned out through the opening 7 according to FIGS. 12A, B, and the capillary 6a according to FIG. 12B. With the circular portion also the space in the receiving vessels like centrifuge tubes and deep well plates is utilized better since the deep well plates typically also taper in a U-shape or in a V-shape. The membrane is typically made from regenerated cellulose, however it can also be made from the materials listed in the general description provided supra individually or in combination.

Plural reaction vessels can also be arranged in a bar shape. The embodiments of the reaction vessels 1 through 5 can be arranged one after another in bar shape so that they are inserted in microplates according to the SBS standard (FIGS. 5A-C; FIGS. 6A-C). The number of reaction vessels per bar can be 2 through 24. Optionally a permanent connection can be provided with or without rated fracture joints 22 according to FIG. 13. The base elements are provided in this case in bar shape, e.g. through injection molding. This facilitates a simple production of plural reaction vessels in one step. Handling plural reaction vessels for example when inserting them into a deep well plate is possible. A user can easily separate a desired number at the rated fracture joints 22 (see FIG. 13). It is optionally feasible to provide the connection of the reaction vessels in the upper portion by disengageable form locking connection, e.g. dove tails (FIGS. 5A-C, 9A, B, 10A, B) or alignment pins. The disengageable connection facilitates to plug together any number of reaction vessels in bar shape according to the SBS standard for microplates.

Figure 7:
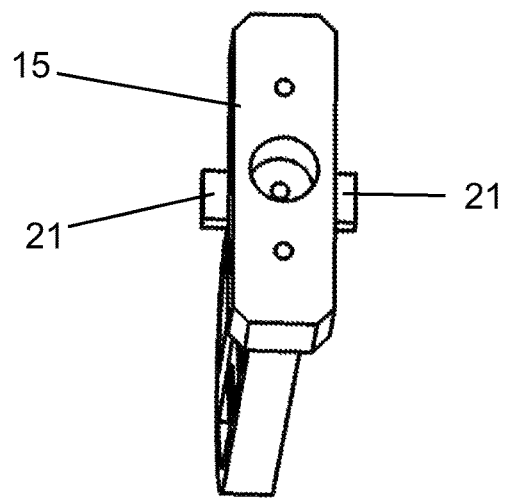
FIG. 7 illustrates exemplary positioning aides at the reaction vessel.

For a safe positioning of the reaction vessels or the bars made from plural reaction vessels in the vessels optional lateral positioning elements 21 can be arranged in upper portions of the reaction vessels (see FIG. 7). The positioning elements are used as spacers from the wall of the respective receiving vessel. They are sized for example when centrally inserted into deep well plates so that they support the inserted reaction vessel exactly in a center between opposite walls when they contact a wall of the receiving vessel.

The dimensions and sizes of the arrangements described herein, their masses and volume capacities are infinitely adaptable. Subsequently a few specifications are recited in an exemplary manner. A first embodiment implements a maximum sample volume of 1,000 µl and has an empty mass of 1.4 g. The base element of the reaction vessel respectively has a width of approximately 20 mm, a length of approximately 50 mm and a thickness of approximately 10 mm at the most in the portion of the fill-in openings. A cartridge is made for example from six base elements connected by the connection elements 9 and 10 in FIGS. 10, 11, 12.

This arrangement is usable up to a temperature of 70 degrees C. at the most and mostly provided for watery solutions with a pH value of 3 to 10. The cutoff for the relative molecule masses that are capable of diffusing through the membrane is 3 to 5, 6 to 8, or 12 to 14 kDa depending on the membrane material. Besides the batteries with six cartridges of six base elements each, the batteries can be scaled to fit one to 48 samples.

Feasible applications are cleaning protein and/or peptide samples, in particular a desalinization before using mass spectrometer analysis methods, optimizing protein renaturalizations with various buffer solutions, removing colorants after a protein labeling or a buffering of a protein sample. By the same token, a modification of glycoproteins and their handling and in vitro translations of proteins can be performed. An enzymatic activity test or a plasmid or primer cleaning.

The invention claimed is:

1. A reaction vessel comprising:
   (1) a frame of annular shape and sidewalls affixed to the frame to form a reaction cavity, wherein the frame comprises lateral beams which merge in a U-shape to form a lower wall of the reaction cavity and upper extremities of the lateral beams are bridged by a member to form an upper wall of the reaction cavity and each of the sidewalls is formed by a respective semipermeable membrane affixed to the frame, the reaction vessel being configured to be received and operate in a vertical operating position in a standard receiving vessel and thereby provide an outer volume formed by and between an exterior of the reaction vessel and an interior of the standard receiving vessel;
   (2) at least one first opening formed through the upper wall of the reaction cavity and provided with a reversible sealing seal element, the at least one first opening being configured to communicate between the outer volume and the reaction cavity for filling, emptying, mixing and gassing of a sample;
   (3) at least one second opening formed through the upper wall of the reaction cavity and being configured to communicate between the outer volume and the reaction cavity for pressure balancing and overrun of a sample;
   (4) a capillary channel formed in one of the lateral beams, the capillary channel being configured to communicate with one of the at least one first opening and having an end opening in the lower wall of the reaction cavity; and
   (5) an outlet opening formed through the lower wall of the reaction cavity and configured to communicate between the outer volume and the cavity and with the end opening of the capillary channel.

2. The reaction vessel according to claim 1, wherein the lower opening connects the capillary channel to the inner cavity.

3. The reaction vessel according to claim 1, comprising two capillary channels and two lower openings,
   wherein each of the two capillary channels vertically connects one of the at least one first upper openings with one of the two lower openings, and
   wherein one of the two lower openings connects one of the two capillary channels to the inner cavity, and the other of the two lower openings connects the other of the two capillary channels to the outer volume.

4. The reaction vessel according to claim 1, comprising three capillary channels and three lower openings
   wherein each of the three capillary channels vertically connects one of the at least one first upper openings with one of the three lower openings, and
   wherein two of the three lower openings each connects one of the three capillary channels to the inner cavity and the other of the three lower openings connects the other of the three capillary channels to the outer volume.

5. The reaction vessel according to claim 1, comprising two capillary channels and two lower openings,
   wherein each of the two capillary channels vertically connects one of the at least one first upper openings with one of the two lower openings, and
   wherein the two lower openings each connects a respective one of the two capillary channels to the inner cavity.

6. The reaction vessel according to claim 1, wherein the lower opening is arranged directly above a base of the receiving vessel at a distance of 0.3 mm to 3 mm, so that the lower opening is not closed by the base of the receiving vessel.

7. The reaction vessel according to claim 1, wherein the one or more capillary channels each comprise a fine pore frit at the lower portion of the reaction vessel.

8. The reaction vessel according to claim 1, wherein the capillary channel is formed entirely in the frame.

9. The reaction vessel according to claim 1, wherein the capillary channel is formed in the frame together with one of the semipermeable membranes.

10. The reaction vessel according to claim 1, wherein each of the semipermeable membranes is made from one or more materials selected from the group consisting of regenerated cellulose, polyethersulfone, polyethylene, cellulose ester, silicone, glass fibers, and ion dotted materials.

11. The reaction vessel according to claim 10, wherein each of the semipermeable membranes is made from at least two different materials selected from the group consisting of regenerated cellulose, polyestersulfone, polyethylene, cellulose ester, silicone, glass fibers, and ion dotted materials.

12. An assembly comprising at least two reaction vessels according to claim 1, wherein the at least two reaction vessels are arranged in series in a bar with the outlet opening of each reaction vessel arranged in a plane in a configuration of a grid of micro plates according to Society of Biomolecular Screening (SBS) micro plate standard at a distance of n.times.9 mm for n=1-12.

13. An assembly comprising two to, twenty-four reaction vessels according to claim 1, wherein the two to twenty-four reaction vessels are connected in upper portions thereof in one plane and are arranged in a configuration of a grid of micro plates according to SBS micro plate standard so that they can be inserted with their lower portions into the micro plates.

14. An assembly comprising at least two of the reaction vessels according to claim 1, wherein the at least two reaction vessels are connected with one another with their upper portions in a plane with reversible form locking connections and are arranged in a configuration of a grid of micro plates according to SBS micro plate standard so that they can be inserted with a lower portion into the micro plates.

15. The reaction vessel according to claim 1, further comprising positioning elements positioned in an upper portion of the reaction vessel, said positioning elements being configured to fixate the reaction vessel within a SBS micro plate standard grid in a position in a respective well of the micro plate.

16. The reaction vessel according to claim 1, wherein the standard receiving vessel providing an outer volume is a centrifuge tube, micro plates or deep well plates.

17. The reaction vessel according to claim 10, wherein the semipermeable membrane material comprises ion dotted materials.

18. The reaction vessel according to claim 11, wherein the semipermeable membrane material comprises ion dotted materials.

19. The assembly according to claim 14, wherein the reversible form locking connection comprises dove tails and/or pinions.

* * * * *